United States Patent [19]

McGeehan

[11] Patent Number: 4,820,627

[45] Date of Patent: Apr. 11, 1989

[54] METHOD OF PREPARING PARTICLES SUITABLE FOR TABLETTING INTO DIAGNOSTIC REAGENTS

[75] Inventor: John K. McGeehan, Woodbury, N.J.

[73] Assignee: EM Diagnostic Systems, Inc., Gibbstown, N.J.

[21] Appl. No.: 842,968

[22] Filed: Mar. 24, 1986

[51] Int. Cl.$^4$ .............................................. C12Q 1/00
[52] U.S. Cl. .......................................... 435/4; 435/6;
435/7; 435/11; 435/14; 435/15; 435/18;
435/17; 435/21; 435/25; 435/28; 435/317.1;
436/8; 436/174; 436/183; 424/464; 424/465;
34/9; 34/10; 264/121
[58] Field of Search .................... 424/464, 465; 435/4,
435/6, 7, 11, 14, 15, 17, 18, 21, 25, 28; 436/8,
174, 183

[56] References Cited

U.S. PATENT DOCUMENTS

| | | | |
|---|---|---|---|
| 3,413,198 | 11/1968 | Deutsch et al. | |
| 3,451,935 | 6/1969 | Roald et al. | 252/135 |
| 3,539,450 | 11/1970 | Deutsch et al. | |
| 3,687,717 | 8/1972 | Philip et al. | 117/100 |
| 3,687,853 | 8/1972 | Natali et al. | 252/89 |
| 3,721,725 | 3/1973 | Briggs et al. | 264/6 |
| 4,106,991 | 8/1978 | Markussen et al. | |
| 4,242,219 | 12/1980 | Bogerman et al. | 252/174.12 |
| 4,428,973 | 1/1984 | Horner et al. | 427/3 |
| 4,447,527 | 5/1984 | Monte et al. | 425/7 |
| 4,489,026 | 12/1984 | Yalkowsky | 424/465 |
| 4,572,897 | 2/1986 | Amotz et al. | 425/177 |
| 4,578,876 | 4/1986 | Cartwright et al. | 34/10 |
| 4,689,297 | 8/1987 | Good et al. | |

*Primary Examiner*—Sam Rosen
*Attorney, Agent, or Firm*—Millen & White

[57] ABSTRACT

A completely water-soluble, solid, labile biochemical-containing diagnostic reagent is prepared without the need of a lyophilization step, by spraying, preferably by a fluidized bed process, an aqueous solution of labile biochemical, e.g., an enzyme, onto small particles, e.g., lower than 20 mesh, of an inert, completely water-soluble solid bulking agent, e.g., mannitol; drying the resultant labile biochemical-coated bulking agent to the desired dryness; and then forming resultant dried labile biochemical-coated bulking agent into a tablet suitable for a diagnostic test reagent, said tablet having a predetermined rate of dissolution.

42 Claims, No Drawings

METHOD OF PREPARING PARTICLES SUITABLE FOR TABLETTING INTO DIAGNOSTIC REAGENTS

BACKGROUND OF THE INVENTION

This invention relates to the field of diagnostic reagents, and in particular to the production of such reagents which contain at least one labile biochemical, e.g., an antibody, nucleotide or enzyme.

For several decades, diagnostic reagents containing labile biochemicals have been employed to provide an assay for a given analyte in order to provide, for example, information for the diagnosis of pathological disorders. See, for example, U.S. Pat. Nos. 3,413,198, Deutsch, issued Nov. 26, 1968; 3,721,725, Briggs et al, issued Mar. 20, 1973; 4,067,775, Würzburg et al, issued Jan. 10, 1978; and 4,447,527, Monte et al, issued May 8, 1984. In all of these referenced diagnostic reagents, the enzyme was used in a lyophilized condition so that the enzymatic component would not be degraded which would otherwise result in non-uniform and unreliable reagents. The same is true with respect to other degradable components such as, for example, nucleotides and antibodies. Such lyophilized biochemicals were also compounded with each other, e.g., co-enzymes and antibodies, as well as with excipients such as, for example, enzyme stabilizers, bulking agents, buffers, enzyme activators, etc. Heretofore, the components were blended and then formed into larger particles, e.g., tablets, by a variety of means, with the understanding that when diagnostic test tablets are to be employed in automatic clinical analyzers, there is at a minimum a twofold requirement for the tablets—a uniform concentration of diagnostic ingredients therein and a uniform rate of dissolution from tablet to tablet.

In the conventional blending of small amounts of lyophilized enzyme, e.g., not more than 1% by weight of the total, with a bulking agent, e.g., mannitol, it was discovered that the difference in bulk density between the two constituents was so high that deblending of the constituents could occur after the blending step.

An attempt was made to agglomerate the lyophilized enzyme with the bulking agent, e.g., mannitol, by the fluidized bed agglomeration process, but this proved to be unsuccessful. Because the bulk density of the lyophilized enzyme was so low compared to the mannitol, many difficulties occurred during the fluidization process, not the least of which was that the resultant agglomerate was very fragile, resulting in a breakdown of the agglomerate during further handling. Other difficulties included, for example: loss of the light weight lyophilized enzyme in the filters at the top of agglomeration chamber and loss of product clumped in oversized lumps. Furthermore, the process required a relatively high air temperature to drive the moisture from the binder solution, possibly denaturing the enzyme and/or decomposing other labile components.

SUMMARY OF THE INVENTION

One object of this invention, therefore, is to provide an improved method for providing a uniform blend of a small amount of enzyme with a large amount of bulking agent.

Another object of the invention is to provide novel intermediate physical forms incorporating an enzyme, said forms facilitating the tabletting of the enzyme into tablets and the like which will have both a uniform concentration and rate of dissolution.

Still another object is to provide one or more methods for producing said intermediate physical forms.

Still another object of this invention is to provide diagnostic tablets or the like which will fulfill the above-desired requirements as well as a method for producing same.

Still further objects include the application of the above objects to other labile biochemicals, including but not limited to antibodies and nucleotides, especially such biochemicals which heretofore were lyophilized prior to being incorporated to a diagnostic reagent.

Upon further study of the specification and appended claims, further objects and advantages of this invention will become apparent to those skilled in the art.

To attain the objects of this invention, it has been unexpectedly discovered that it is possible to coat particulate bulking agent, e.g., mannitol, with a solution of an enzyme, preferably by a fluidized bed coating process, and that it is unnecessary to utilize a lyophilized enzyme as was heretofore believed necessary for the purposes of producing diagnostic reagents. The resultant coated particulate bulking agent can then be easily formed into tablets having a uniform concentration of constituents as well as a uniform rate of dissolution. Based on this discovery, it was further discovered that other constituents always incorporated heretofore in lyophilized form, especially those incorporated in diagnostic tests, could be successfully coated on a particulate, complete water-soluble bulking agent or the like.

For purposes of the following discussion, such a constituent will be called a "labile biochemical" which is intended to cover, as special embodiments, all enzymes, all antibodies, all coenzymes, all nucleotides and certain substrates.

In the context of the present invention, it is to be further understood that "coating" includes but is not limited to, impregnation into the pores of the particulate bulking agent wherein the pore walls may be coated or filled.

In general, the process for the production of the diagnostic tablet or the like (which can be characterized as a water-soluble, solid, labile biochemical-containing diagnostic reagent) comprises the steps of:

(a) providing an aqueous solution of labile biochemical;

(b) providing particulate, completely water-soluble, inert, preferably non-hygroscopic, solid bulking agent;

(c) atomizing and uniformly spraying said aqueous solution of labile biochemical in the form of fine droplets, in a small amount, over an extended time period, onto said particulate bulking agent, the latter undergoing continuous agitation while in contact with a surrounding gaseous medium, and continuously evaporating water from said aqueous solution of labile biochemical while incorporating said labile biochemical on said particulate bulking agent under conditions effective to provide uniform distribution of said labile biochemical on said particulate bulking agent and to prevent substantial agglomeration of said bulking agent or build-up of substantial wetness in said bulking agent;

(d) drying resultant labile biochemical-coated bulking agent to the desired dryness; and (e) then forming resultant dried labile biochemical-coated bulking agent into a tablet suitable for a diagnostic test reagent, said tablet having a predetermined rate of dissolution.

It is contemplated that in some cases the particulate product from step (d) may also be used directly in a diagnostic test without need of a tabletting step or the like.

As stated above, a discovery of the present invention is that the enzyme or other labile biochemical employed can be one that was never lyophilized. On the other hand, if it is convenient to utilize a lyophilized labile biochemical (for example, it may be in inventory and have no other use), it is also possible to utilize the process of the present invention by dissolving a lyophilized labile biochemical in order to provide the solution set forth in step (a).

According to a preferred embodiment of the present invention, the labile biochemical solution that is provided in step (a), when containing an enzyme, also contains a stabilizer to prevent degradation of the enzyme during the process and thereafter. Such stabilizers include, but are not limited to bovine serum albumin, polyethylene glycol and salts such as sodium chloride and potassium chloride. A particularly outstanding advantage in this connection is that a high concentration of said salts can be employed in order to impart optimum stabilities to certain systems, whereas such high salt concentrations before the present invention could not be lyophilized. For example, it is possible to employ about a 3 molar solution of sodium chloride for a solution containing glucose dehydrogenase and about a 1.5 molar solution of potassium chloride for a solution containing mutarotase, thereby obtaining exceedingly high yields of the enzyme compared to the lyophilization process.

It is furthermore preferred in connection with the invention that the spray solution of step (a) contain a buffer so that the pH is adjustable to the desired value, e.g., in the case of hexokinase, to 7.00 with an average deviation of 0.05. To provide such a buffer solution, it is preferred to employ a monobasic potassium phosphate in deionized water. On the other hand, the particular buffers employed are not critical to the invention and one or another buffer may be employed, depending upon the specific reagents. Again, it is possible to rely on the state-of-the-art, in connection with any particular system. The spray solution may also contain other diagnostic reagents including but not limited to, for example, a mixture of labile biochemicals, e.g., one or more of antibodies, nucleotides, etc., as well as substances which act as solid diluents for the enzyme deposit on the particulate bulking agent.

As for the nature of the bulking agent, it is to be understood that in general, it must be able to achieve complete dissolution in water in under a minute. Accordingly, the term "bulking agent" in this invention is meant to include such diverse cores as pure mannitol on the one hand and a total CK reagent blend on the other hand. Also the term "inert" means that the bulking agent does not adversely interfere with the diagnostic test.

According to a preferred embodiment, the bulking agent is non-hygroscopic to the same degree as mannitol. However, more hygroscopic bulking agents can also be used so long as the degree of hygroscopicity does not interfere with the coating process, i.e., cause agglomeration.

According to another preferred embodiment of the invention, it is beneficial for the particulate bulking agent to have a substantially spherical shape. In this way, the coating process is facilitated, especially when a fluidized bed coating process is used. Furthermore, the resultant substantially spherical particles are advantageous inasmuch as they are free-flowing and in turn facilitate the tabletting operation. Whereas there are a number of spherulization techniques for obtaining spherical shapes, e.g., those set forth in U.S. Pat. No. 4,572,897, col. 6, lines 35-60, it is preferred, in the case of mannitol, to prepare the substantially spherical particles by rotary granulation, especially by the Glatt rotor granulator/coater.

According to still another preferred embodiment of the invention, the bulking agent not only comprises mannitol, but in certain cases, it consists of mannitol, i.e., no other ingredients except impurities are associated therewith. It was unexpected that such a purity of mannitol could be successfully agglomerated and then coated by an enzyme solution inasmuch as pure mannitol is more difficult to agglomerate than mixtures of mannitol with small amounts of sodium chloride, for example.

Aside from the utilization of mannitol as a bulking agent, there are other inert, water-soluble, preferably non-hygroscopic bulking agents, especially organic compounds or mixtures thereof which are set forth in the prior art which will perform substantially the same function as mannitol, and all of these bulking agents are included by reference herein. For example, the bulking agents are preferably polyols, which may be sugars or reduced sugars, monomers or polymers, noting further U.S. Pat. No. 4,447,527, columns 6 and 7, incorporated by reference herein. The particle size of the bulking agent is such that it can be coated by the above defined process, especially by a fluidized bed process. It is preferred that the particle size be within about 20 to 80 mesh, (U.S. sieve size).

According to another embodiment, the bulking agent can comprise mannitol in a low concentration, e.g., about 10%, compared to a high concentration of a buffer system of aspartic acid and sodium aspartate. Conversely, according to another embodiment the bulking agent comprises a high concentration of mannitol, e.g., about 98% and low concentration of bovine serum albumin.

As for the labile biochemicals which can be employed in the present invention, it is contemplated that all labile biochemicals useful for diagnostic reagents can be incorporated, not only those labile biochemicals known heretofore, but those that will be discovered in the future. For exemplary systems, reference is directed to the particular patents which were cited in the "Background of the Invention" portion, supra. In any case, the preferred enzymes of the present invention include but are not limited to reference to α-glucosidase, β-glucosidase, glucose-6-phosphate dehydrogenase, hexokinase, glucose dehydrogenase, mutarotase, cholesterol oxidase, cholesterol esterase, glycerol phosphate oxidase, glycerol kinase, or malate dehydrogenase.

With respect to the coating of antibodies on particulate bulking agents, a highly important antibody is the antibody which inhibits CK-MM in the modern test for determining cardiac infarctions. Other important antibodies are used in drug testing, and solutions of such antibodies can be sprayed onto mannitol or the like in the same manner as the enzymes, with the special purpose of physically separating the antibodies from other reactive components of the test.

As for the coating of coenzymes on bulking agents according to the invention, especially well known in the diagnostic reagent field are flavin mononucleotides, flavine adenine dinucleotide, pyridoxal 5' phosphate and diadenosine pentaphosphate.

With respect to the coating of nucleotides on particulate bulking agents, examples of nucleotides contemplated for diagnostic use, include but are not limited to: adenosine monophosphate, adenosine diphosphate, adenosine triphosphate, guanosine monophosphate, uridine monophosphate, cytidine monophosphate, deoxyadenosine monophosphate deoxyguanosine monophosphate, deoxythymidine monophosphate, and deoxycytidine monophosphate.

With respect to the coating of labile substrates on particulate bulking agents, examples of labile substrates contemplated for diagnostic uses, include but are not limited to: p-nitrophenyl derivatized dextrans, α-ketoglutarate, glucose-6-phosphate, phosphoenol pyruvate, glyceraldehyde-3-phosphate and fructose-6-phosphate.

In any case, it is clear that this invention is applicable to coating with a solution of any labile biochemical, including all antibodies, all enzymes, all coenzymes, and all nucleotides, as well as certain substrates that are degradable because of temperature and/or moisture considerations.

As for the concentration of a given labile biochemical to be incorporated on a given particulate bulking agent, this will vary in accordance with the requirement of the specific diagnostic test. For representative and preferred concentrations, reference is made to the following table:

| Test | Labile Biochemical (LB) | Base Granulation | Minimum % LB* | Maximum % LB* |
|---|---|---|---|---|
| Amylase | α-glucosidase | mannitol seed (60–80 M) | 7 | 22 (10%)** |
|  | β-glucosidase | mannitol seed (60–80 M) | 3 | 22 (10) |
| Creatine Kinase | Glucose-6-Phosphate Dehydrogenase | mannitol seed (40–60 M) | 0.09 | 20 (10) |
|  | Hexokinase | mannitol seed (40–60 M) | 0.6 | 20 (10) |
| Creatine Kinase-MB | CK-M inhibiting Antibody | total CK reagent blend | 0.7 | 21 (10) |
| Glucose | Glucose Dehydrogenase | mannitol seed (40–60 M) | 0.9 | 14 (10) |
|  | Mutarotase | mannitol seed (40–60 M) | 0.8 | 13 (10) |
|  | Nicotinamide Adenine Dinucleotide | mannitol seed (40–60 M) | 6 | 20 (10) |
| Cholesterol | Cholestrol Oxidase | mannitol-BSA co-granules | 0.2 | 20 (10) |
|  | Cholesterol Esterase | mannitol-BSA co-granules | 0.2 | 20 (10) |
| Triglycerides | Glycerol Phosphate Oxidase | mannitol-BSA co-granules | 1.5 | 20 (10) |
|  | Glycerol Kinase | mannitol-BSA co-granules | 0.1 | 20 (10) |
| Aspartate Amino Transferase | Malate Dehydrogenase | mannitol-LDH co-granulation |  |  |
|  | Nicotinamide Adenine Dinucleotide (reduced) | mannitol seed (20–60 M) | 0.8 | 20 (10) |
|  | Pyridoxal 5' Phosphate | mannitol-aspartic acid co-granules | 0.3 | 20 (10) |

BSA = bovine serum albumin
M = mesh size (U.S. sieve)
*approximate percent by weight of labile biochemical based on total particle
**number in parentheses represents preferred maximum As indicated below, it is preferred to employ polyethylene glycol as a lubricating agent, and it is employed in a sufficient amount to provide lubrication during tabletting but not so much as to increase the mesh sizes significantly. Thus, a coating of about preferably 0.75–1.5%, especially about 1% by weight of PEG is employed. Whereas PEG having lower molecular weights are contemplated, a PEG having a molecular weight of 20,000 is preferred inasmuch as it is likely to afford a greater protection against abrasion of the particle.

Of particular importance are systems wherein the mannitol has a particle size of 40–60 mesh and the enzyme is glucose-6-phosphate dehydrogenase or hexokinase on the one hand, or glucose dehydrogenase or mutarotase on the other hand.

From the standpoint of uniformity, it is desirable to provide particles having a uniformity such that the resultant tablets have a coefficient of variation of less than five percent with respect to labile biochemical concentration, and this invention provides such uniformities.

After the particulate bulking agent is coated with enzyme, according to another embodiment of the invention, the resultant particulate solid is coated with one or more layers of additional excipients which assist in the tabletting operation and/or the diagnostic test itself.

For example, it is contemplated to add a layer of lubricant, such as, for example, polyethylene glycol, preferably polyethylene glycol 20,000, to aid in tabletting and to minimize abrasion, as well as to protect the enzyme from breaking off from the particulate bulking reagent during the processing thereof. It has been unexpectedly discovered that such a coating may be successfully applied directly after the enzyme coating step with no intermediate step of drying; however, the coating may, of course, be applied after a drying step as well. Another example is to provide a coating having a given dissolution rate, thereby providing a predetermined time - dissolution characteristic for the resultant product, and in the same way, a pH dependent coating is contemplated such that the enzyme will be released only at a specific pH. In addition, according to another embodiment of the invention, other constituents for the test may be coated separately onto the particle, e.g., another biochemical, etc.

According to a particularly preferred embodiment of the process of the invention, fluidized bed coating is employed in order to coat the bulking agent with the enzyme. In this connection, fluidized bed coating has been utilized in a wide variety of industries. However, because of the perceived need for lyophilization of labile biochemicals in the diagnostic reagent field and the proven operability of known procedures, the application of a fluidized bed coating technique was, prior to the present invention apparently never even considered. Furthermore, even it were considered, it is believed that a worker in this field would have concluded that since the particulate bulking material must be completely water-soluble, a fluidized bed coating process could not be satisfactory. The reason for this is that because the labile biochemical is sprayed in an aqueous media, it would be probable that the aqueous media could attack the surface of the particulate water-soluble bulking agent, resulting in a sticky surface and undesirable clumping of particles rather than the desired coated free-flowing particles. Indeed, such appeared to be the case when fluidized agglomeration was attempted with lyophilized enzyme. Thus, the success of a fluidized bed coating process in the invention is quite remarkable.

With respect to the details of the fluidized bed coating process, there are many known variables which must be adjusted in order to arrive at optimum results. For example, the variables include: the nature of the particulate bulking agent, including physical characteristics, particle size and affinity for the materials being sprayed; the particular coating solution, including not only the specific labile biochemical included therein, but also its concentration as well as any excipients. These "product variables" in turn interrelate with the process variables which include, for example, the atomization air pressure for the nozzle, the liquid spray rate, the fluidization air temperature and humidity, the fluidization air velocity, etc.

As applied to the present invention, these variables may be customized for any particular system, and through routine experimentation, optimum results can be obtained.

For the purposes of the present invention, the following guidelines will be helpful to obtain optimum results for any given system:

With respect to the coating time of the fluidized bed coating process, it has been found, for example, that during an enzyme coating process of mannitol, that 30–60 minutes is preferred. When longer coating times were employed, it was found that some abrasion occurred which resulted in a removal of the enzyme material from the mannitol.

In the final analysis, it is also important to prevent substantial agglomeration during the process, generally meaning that during the coating of the labile biochemical, less than about 1% of agglomeration is obtained. (It is to be noted, however, that when polyethyleneglycol was used as the coating agent, some agglomerates were formed which were very easily breakable. Thus, it was preferred to force the resultant product after a polyethylene glycol coating operation through a 40 mesh screen.)

As for moisture conditions, it was found to be preferable to utilize dry air, e.g., having a relative humidity at 20° C. of 4% or less, for fluidization. Likewise, it is important to avoid substantial wetness of the particles during the coating operation; for example, it is preferred for the coated particulate solids to contain not more than about 10% moisture by weight.

Inasmuch as it is desired to vaporize each drop of fluid as it is deposited on the particulate bulking agent, before the next drop of fluid enters, there is an interrelationship between the fluidization air velocity on the one hand and the liquid spray rate and degree of atomization of the droplets on the other hand. Other factors include the fluidization air temperature and humidity as well as the characteristics of the particular spray nozzle employed.

With respect to the concentration of the constituents in the spray solution, it is desirable that as concentrated a solution as possible be employed so that the minimum amount of water will enter into the fluidization process. As more water enters into the process, it becomes necessary to employ longer drying times and/or higher temperatures. On the other hand, it is important that the concentration be not so high as to result in premature precipitation of the constituents prior to being captured by the particulate bulking agent. It is also desirable for the spray solution to be stored at a low temperature so as not to denature the labile biochemical, e.g., 4° C.

All of the above factors go the optimization of the process rather than to the operability of same.

With respect to the nature of the "product variables", it is important for the purposes of this invention for the resultant diagnostic reagent tablet to dissolve in the analyte solution as rapidly as possible so that the assay determination can then be conducted without delay. Generally, the laboratory reagent will dissolve in less than one minute. For specific dissolution times of specific diagnostic reagent tablets, attention is invited to the specifications that are in use today, and if not published, are well known to those working in this field, and such information is incorporated by reference herein.

Inasmuch as it was not at all predictable that the present invention would be operable, a microscopic examination was made of an enzyme-coated mannitol product wherein the enzyme concentration was about 1% by weight. The enzyme coating was not discernible. Thereupon, a dye solution was substituted for the enzyme solution, all other things being equal. Even so, one could not observe the dye on the resultant particle. In this connection, the particulate mannitol employed is necessarily porous because it is an agglomerate, and without being bound by the mechanism of the invention, it is believed that a substantial quantity of the finely atomized droplets are captured within the pores of the particulate bulking agent. Because the outer surface of the particulate bulking agent is not accessibly wetted, little or no sticky film is formed which might otherwise result in a deleterious agglomeration of particles. Accordingly, the fact that the particulate bulking agent is of a porous nature is believed to contribute to the unexpected success of the present invention.

It is to be appreciated that once a worker in this field has knowledge that it is possible to utilize the fluidized bed coating technique or the like, and omit the energy-intensive, equipment-intensive, and time-consuming lyophilization step in the production of diagnostic regents, the worker will be able to utilize the present invention with a wide variety of particulate bulking agents and labile biochemicals. In other words, once the feasibility of the present process is appreciated, it will be merely a matter of routine experimentation to develop a given optimum process for any given system.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following preferred specific embodiments of the invention, all temperatures are set forth uncorrected in degrees Centigrade and all parts and percentages are by weight unless otherwise indicated. The mesh sizes refer to U.S. sieve sizes.

EXAMPLE 1

A. Preparation of Mannitol Seeds, i.e., Particulate Bulking Agent

A Glatt GPCG-5 fluid bed granulator is used for the process using the rotary granulator insert and auxiliary equipment supplied as standard equipment by Glatt.

The product container of the unit is charged with 5 kg of mannitol which has previously been sized to less than 80 mesh. A solution of 8% polyvinyl pyrrolidone (molecular weight=40,000) and 2% polyethylene glycol (molecular weight=20,000) w/v was prepared for use as a binder solution for the agglomeration process.

The mannitol was agglomerated in the rotary granulator (following standard operating procedures from Glatt) using the following parameters:
Binder solution flow rate=75 ml/min
Atomization air pressure=2 bar
Volume of binder solution=1800 ml
Granulation temperature=30 degrees C.
Rotor speed=250–300 rpm Following completion of spraying of the binder solution, the rotor speed is reduced to prevent particle attrition and the granulation is dried at a temperature of 60° C. to less than 1% moisture content.

The resulting granulation is sieved to select the fraction between 40 and 60 mesh. This resultant 40 to 60 mesh mannitol granulation is used as seeds, i.e., particulate bulking agents, upon which solutions containing enzymes, nucleotides, antibodies, etc., are sprayed.

B. The following enzyme solutions were used to coat the bulking agent:

| 1. Mutarotase Solution | |
|---|---|
| Ingredients: | |
| Potassium chloride | 74.6 g |
| Polyethylene glycol-20,000 | 22.5 g |

| 1. Mutarotase Solution (continued) | |
|---|---|
| Ingredients: | |
| Bovine serum albumin | 50.0 g |
| Deionized Water | 1000 ml |

160,000 units of lyophilized mutarotase were dissolved in 720 ml of the above solution.

| 2. Glucose Dehydrogenase Solution | |
|---|---|
| Ingredients: | |
| Sodium chloride | 175 g |
| Polyethylene glycol-20,000 | 20 g |
| Deionized Water | 1000 ml |

8,970,000 units of lyophilized glucose dehydrogenase were dissolved in 960 ml of the above solution.

| 3. Glucose-6-phosphate dehydrogenase Solution | |
|---|---|
| Ingredients: | |
| Bovine serum albumin | 150 g |
| 0.02 M Potassium phosphate buffer (pH 7.0) | 900 ml |

3,000,000 units (4.58 g) of lyophilized glucose-6-phosphate dehydrogenase were dissolved in 900 ml of the above solution.

| 4. Hexokinase Solution | |
|---|---|
| Ingredients: | |
| Bovine serum albumin | 90 g |
| 0.02 M Potassium phosphate buffer, pH 7.0 | 540 ml |

1,500,000 units (19.87 g) of lyophilized hexokinase were dissolved in 540 ml of the above solution.

C. Fluid Bed Enzyme Coating

The mutarotase solution, glucose dehydrogenase solution and glucose-6-phosphate dehydrogenase solutions at a temperature of about 4° C. were sprayed onto separate 5 kg charges of the mannitol seeds (described in A above) using the following process.

A Glatt GPCG-5 fluid bed granulator having a size 12 nozzle is used for the process using the standard product container and auxiliary equipment supplied as standard equipment by Glatt.

The enzyme solutions were sprayed onto a fluidized bed of the mannitol seeds using the following parameters:
Enzyme solution flow rate: 30 ml/min
Atomization air pressure: 2.5 bar
Coating temperature: 38° C.
Fluidization air humidity: 4% RH The hexokinase solution was sprayed onto 3 kg of mannitol seeds using the above process.

Immediately after spraying the enzyme solutions onto the mannitol seeds, a solution of 20% polyethylene glycol-20,000 was sprayed onto the enzyme coated mannitol seeds.

The granulations were then dried to a moisture content of less than 1% using 38° C. fluidization air with a relative humidity of approximately 4%.

A comparison of bulk density between lyophilized hexokinase and the hexokinase spray coated on mannitol was performed by two methods. First, the lyophilized hexokinase and the spray coated hexokinase were each poured into tared 25 ml glass graduated cylinders. The volume and weight of each was recorded to determine the loose packed bulk density. Both graduated cylinders were then clamped in a Thomas vibrating sieve shaker and vibrated at full amplitude for 2 minutes to obtain a dense packed volume. Each volume was divided by the weight of the respective material to determine the bulk density.

|  | Lyophilized Hexokinase | Hexokinase Coated on Mannitol |
| --- | --- | --- |
| Loose Packed bulk density | 0.0775 g/cc | 0.660 g/cc |
| Dense Packed bulk density | 0.1180 g/cc | 0.749 g/cc |

The loose packed bulk density of the hexokinase coated on mannitol was 8.5 times greater than that of the lyophilized material. The dense packed bulk density of the hexokinase coated on mannitol was 6.3 times greater than that of the lyophilized material.

The lyophilized hexokinase was also compared to the hexokinase coated on mannitol with respect to powder flow. Good powder flow properties are generally essential in order to obtain tablet weight coefficient of variations of less than 1%. Powder flow measurements were obtained by placing the respective materials in a 100 cc plastic graduated cylinder which had the bottom cut out and replaced with a tablet press die (7/32" diameter punch size). A piece of tape was placed over the hole in the die at the bottom to prevent the flow of powder until ready for measurement. Powder flow rates were monitored by the change in weight recorded by a Sartorius 1404 balance connected to an Epson HX-20 computer. A program was written for the Epson HX-20 in BASIC so that the weight was printed each second as the powder flows from the graduated cylinder through the hole in the die and onto the balance pan. No sustained powder flow through the die could initiated for the lyophilized hexokinase. The hexokinase coated on mannitol exhibited an average powder flow rate of 6 grams per second using the apparatus above.

D. Use of Enzyme Coated Mannitol Seed in Diagnostic Tests.

The glucose dehydrogenase and mutarotase granulations (prepared as described in step C) were blended with an NAD (nicotinamide adenine dinucleotide) granulation and a tris(hydroxymethyl)aminomethane granulation which were prepared using standard fluid bed granulator agglomeration processes. The resulting blend of granulations comprised the complete chemistry for the measurement of glucose by standard spectrophotometric methodology. The blend of granulations was tabletted on a Stokes Rotary Tablet press using a standard feed frame and metering hopper, with standard modifications made to the press by Stokes-Penwalt to provide a twisting punch mechanism.

The hexokinase and glucose-6-phosphate dehydrogenase granulations (prepared as described in step C) were blended with: (1) a buffer granulation containing Bis-Tris [2,2 bis-(hydroxymethyl)-2,2'''-nitrilo-triethanol], N-acetylcystine, dextrose, EDTA and magnesium acetate (this buffer granulation was prepared using standard rotary granulator agglomeration processes, followed by coating with the non-ionic surfactant Brij-35 in a manner similar to the polyethylene glycol described in C above); (2) a creatine phosphate/mannitol granulation agglomerated by standard fluid bed methods; and 3) a co-enzyme granulation composed of AMP (adenosine mono-phosphate), ADP (adenosine diphosphate), NADP (nicotinamide adenosine dinucleotide phosphate) and mannitol agglomerated by standard rotary granulation methods. The resulting blend of granulations comprised the complete chemistry for the measurement of creatine kinase by standard spectrophotometric methodology. The blend of granulations were tabletted by the same methods as described for the glucose test above.

EXAMPLE 2

This coating process can also be employed for spraying CK-MM inhibiting antibody onto a blend of the granulations for the creatine kinase test (described above) prior to tabletting. The process to be utilized is the same as described for the fluid bed enzyme coating in part C above. The use of this process will uniformly distribute the antibody (dissolved in a 0.5% sodium chloride - 4% Bovine serum albumin solution) throughout the various granulations used in the CK-MB test.

EXAMPLE 3

This process can also be employed to coat nucleotides such as NAD (oxidized and reduced) on the mannitol seeds (in the same manner as the previously described enzymes) in order to increase the bulk density of the raw material. This increase in bulk density improves the homogeneity of the NAD in a granulation (C.V. re tablet weight=2 to 3%) when compared to agglomeration of lyophilized NAD and mannitol (C.V.=4 to 8%) by standard methods of fluid bed granulation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a completely water-soluble, solid, labile biochemical-containing diagnostic reagent, comprising the steps of:
    (a) providing an aqueous solution of labile biochemical;
    (b) providing particulate, inert, completely water-soluble solid bulking agent;
    (c) atomizing and uniformly spraying said aqueous solution of labile biochemical in the form of fine droplets, in a small amount, over an extended time period, onto said particulate bulking agent, the latter undergoing continuous agitation while in contact with a surrounding gaseous medium, and continuously evaporating water from said aqueous solution of labile biochemical while incorporating said labile biochemical on said particulate bulking agent under conditions effective to provide uniform distribution of said labile biochemical on said particulate bulking agent and to prevent substantial agglomeration of said bulking agent or build-up of substantial wetness in said bulking agent;

(d) drying resultant labile biochemical-coated bulking agent to the desired dryness; and (e) then forming resultant dried labile biochemical-coated bulking agent into a tablet suitable for a diagnostic test reagent, said tablet having a predetermined rate of dissolution.

2. A process according to claim 1, wherein said labile biochemical was never lyophilized.

3. A process according to claim 1, wherein said labile biochemical comprises an enzyme.

4. A process according to claim 1, wherein said labile biochemical comprises an antibody.

5. A process according to claim 1, wherein said labile biochemical comprises a coenzyme.

6. A process according to claim 1, wherein said labile biochemical comprises an nucleotide.

7. A process according to claim 1, wherein said solution of labile biochemical contains an enzyme and a stabilizer to prevent degradation of the enzyme during the process.

8. A process according to claim 1, wherein said particulate bulking agent is non-hygroscopic and substantially spherical in shape.

9. A process according to claim 1, wherein said particulate bulking agent comprises mannitol.

10. A process according to claim 1, wherein said particulate bulking agent consists of mannitol.

11. A process according to claim 9, wherein said labile biochemical is α-glucosidase, β-glucosidase, glucose-6-phosphate dehydrogenase, hexokinase, glucose dehydrogenase, mutarotase, cholesterol oxidase, cholesterol esterase, glycerol phosphate oxidase, glycerol kinase or malate dehydrogenase.

12. A process according to claim 10, wherein said enzyme is α-glucosidase, β-glucosidase, glucose-6-phosphate dehydrogenase, hexokinase, glucose dehydrogenase or mutarotase.

13. A process according to claim 3, wherein said particulate bulking agent consists essentially of mannitol having a particle size of 40–60 mesh, and wherein said enzyme is glucose-6-phosphate dehydrogenase or hexokinase.

14. A process according to claim 3, wherein said particulate bulking agent consists essentially of mannitol having a particle size of about 40–60 mesh and wherein said enzyme is glucose dehydrogenase or mutarotase.

15. A process according to claim 4, wherein said antibody is a CK-M inhibiting antibody.

16. A process according to claim 5, wherein said coenzyme is pyridoxal 5' phosphate and the bulking agent comprises cogranules of mannitol and aspartic acid.

17. A process according to claim 6, wherein the nucleotide is nicotinamide adenine dinucleotide and the bulking agent comprises mannitol.

18. A process according to claim 1, further comprising providing a solution of polyethylene glycol 20,000 and intermediate steps (c) and (d) coating the resultant labile biochemical-coated particulate bulking agent with said solution.

19. A product as produced by the process of claim 1.

20. In a method of conducting a diagnostic test which comprises dissolving a diagnostic reagent in an analyte and ascertaining from the physical characteristics from the resultant solution, the assay of said analyte, the improvement which comprises employing as said diagnostic reagent, the product according to claim 19.

21. A process according to claim 1, wherein said labile biochemical is a substrate.

22. A process according to claim 21, wherein said substrate is p-nitrophenyl derivatized dextrans, α-ketoglutarate, glucose-6-phosphate, phosphoenol pyruvate, glyceraldehyde-3-phosphate or fructose-6-phosphate.

23. A product as produced by the process of claim 2.
24. A product as produced by the process of claim 3.
25. A product as produced by the process of claim 4.
26. A product as produced by the process of claim 5.
27. A product as produced by the process of claim 6.
28. A product as produced by the process of claim 7.
29. A product as produced by the process of claim 8.
30. A product as produced by the process of claim 9.
31. A product as produced by the process of claim 10.
32. A product as produced by the process of claim 11.
33. A product as produced by the process of claim 12.
34. A product as produced by the process of claim 13.
35. A product as produced by the process of claim 14.
36. A product as produced by the process of claim 15.
37. A product as produced by the process of claim 16.
38. A product as produced by the process of claim 17.
39. A product as produced by the process of claim 18.
40. A product as produced by the process of claim 21.
41. A product as produced by the process of claim 22.

42. In the tabletting granulation of a diagnostic reagent comprising the steps of passing particulate material to a tabletting machine and then tabletting the particulate material, the improvement which comprises employing at least in part a product produced by a process comprising the steps of:

(a) providing an aqueous solution of labile biochemical;

(b) providing particulate, inert, non-hygroscopic, completely water-soluble solid bulking agent;

(C) atomizing and uniformly spraying said aqueous solution of labile biochemical in the form of fine droplets, in a small amount, over an extended time period, onto said particulate bulking agent, the latter undergoing continuous agitation while in contact with a surrounding gaseous medium, and continuously evaporating water from said aqueous solution of labile biochemical while incorporating said labile biochemical on said particulate bulking agent under conditions effective to provide uniform distribution of said labile biochemical on said particulate bulking agent and to prevent substantial agglomeration of said bulking agent or build-up of substantial wetness in said bulking agent; and (d) drying resultant labile biochemical-coated bulking agent to the desired dryness.

* * * * *